US00PP11525P

United States Patent [19]

Twomey

[11] Patent Number: Plant 11,525

[45] Date of Patent: Sep. 26, 2000

[54] HYBRID TEA ROSE PLANT NAMED 'TWOAEBI'

[76] Inventor: Jerry Twomey, 194 Avocado St., Leucadia, Calif. 92024

[21] Appl. No.: 09/220,904

[22] Filed: Dec. 24, 1998

[51] Int. Cl.[7] ..... A01H 5/00

[52] U.S. Cl. ..... Plt./135

[58] Field of Search ..... Plt./135, 136, 146, Plt./147

[56] References Cited

U.S. PATENT DOCUMENTS

P.P. 4,330 11/1978 Delbard ..... Plt./146

*Primary Examiner*—Howard J. Locker

[57] ABSTRACT

A new rose cultivar of the Hybrid Tea class characterized by having a very double, very long lasting, non-fading, orange flower, with very consistent blooms. This plant has been designated as 'TWOAEBI'. It is being marketed in the USA under the tradename of 'Dream Orange'.

1 Drawing Sheet

The present invention relates to a new and distinctive cultivar of rose plant of the Hybrid Tea class, which was originated by my crossing 'Cherish' as the seed parent with the pollen parent an un-named seedling.

Among the novel characteristics possessed by the new cultivar which distinguish it from:

(a) All other cultivars of which I am aware are: (1) Does well as both a garden and greenhouse rose. (2) Very long lasting. (3) Consistent free bloomer. (4) Yon-fading orange flower.

(b)

*Seed parent.*—Coral/pink, cluster flowered, Floribunda.
*Pollen parent.*—Red flowered, Floribunda.

Asexual reproduction of the new rose cultivar by budding, as performed at Wasco, Calif. shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

Parentage:

*Seed parent.*—'Cherish', U.S. Plant Pat. No. 4,331.
*Pollen parent.*—Seedling — (Evening Star× Trumpeter).

Class: Hybrid Teas.

The following observations are made of specimens grown outdoors in Monterey County, Calif., in the month of August, 1998.

FLOWER

Blooming habit:

A. Bud:

(1) *Size.*—Sepals enclosed, 20–22 mm from base of sepals to top of bud.

(2) *Form.*—Ovoid.

(3) *Sepals.*—28 to 32 mm in length; 8 to 9 mm extension beyond bud; no serration shown on sepal edges. Generally 3 out of 5 sepals show appendages on each side, 2 to 5 mm length. Sepals show glandular development on edges. Heavy cotton matting on inner surface, fine matting on outer surface. Outside color — 147B with shadings of 175A; inside — 196A.

(4) *Peduncle.*—Length — 6 to 6.5 cm. Surface — smooth, no prickles, a few glandular hairs. Strength — firm. Color — 146C, shaded — 175A.

(5) *Receptacle.*—Shape — Oblong, 8–10 mm diameter. Color — 146C.

(6) *Color.*—When sepals first divide, outside petals near to 33B.

B. Bloom:

(1) *Size.*—When open — 8.5 to 9.5 cm.

(2) *Borne.*—1 per stem.

(3) *Form.*—Globular.

(4) *Petalage.*—Average — 34 to 38.

(5) *Color.*—Early open: outer petals near 32B (both surfaces), base 10D; inner petals near 33B (both surfaces). Aging: Near 40D, base 8D.

C. Petals:

(1) *Texture.*—Firm.

(2) *Appearance.*—Flexed; satiny.

(3) *Form.*—Ruffled.

(4) *Arrangement.*—Semi regular and fluted.

(5) *Petaloids in center.*—Average 8 to 10.

(6) *Persistence.*—Petals persist.

(7) *Fragrance.*—Strong.

(8) *Lasting quality.*—On plant 14–16 days; cut 13–14 days.

REPRODUCTIVE ORGANS

A. Stamen:

(1) *Arrangement.*—Regular around styles.

(2) *Number.*—Average 90–100.

(3) *Length.*—Average — 4 to 7 mm from base.

(4) *Filaments.*—Color — Close to 50B.

(5) *Anthers.*—Color — Close to 8C.

(6) *Pollen.*—Color — Close to 8C.

B. Pistil:

(1) *Styles.*—Length: 6–9 mm from center of ovary; number: 115 to 120; color: near to 61A; sparsely coated with white hairs.

(2) *Stigma.*—Color — Close to 157C.

(3) *Ovary.*—Shape — oblong; 7–9 mm center cross section at sepal base.

C. Hips: Does not set seed.

PLANT

A. Form: Upright.

B. Growth: Very Vigorous; Height: average 1½–2 m.

C. Stem length: Basal break to flower bud tip: average — 1½ m.

D. Foliage: Compound of 3 to 5 leaflets on bloom stem; 5 to 7 leaflets on main canes.

(1) *Mature size.*—5 leaflet — tip of leaflet to stipule base 12.5–14 cm.

(2) *Quantity.*—Stems well covered.

(3) *Color.*—New foliage upper side close to 137C; under side near 137D. Old foliage upper side near to 137A, under side near to 137B.

(4) *Shape.*—Oval with center pointed, (5) *Texture.*—Very firm, very leathery.

(6) *Edge.*—Pronounced serration on outer edge. Average 4–5 points per 1 cm, with up to 1–2 mm peak.

(7) *Rachis.*—Glandular hair on lower and upper side; few prickles on lower side: 2 mm length, hooked, 3–4 cm spacing.

(8) *Stipules.*—Length 22–25 mm; auricle to 4–5 mm. Edge of stipule to tip of auricle with few glandular hairs.

E. Resistance to disease: Powdery mildew, rust and blackspot: Good.

F. Wood:

*New wood.*—Color close to 146C, shades of 183B; Bark — smooth.

*Old wood.*—Color close to 146A; Bark — smooth.

G. Thorns on mature wood:

*Size.*—3–4 mm.

*Number per 10 cm.*—Primary wood 5–6 thorns; Secondary wood same.

*Shape.*—Small, very slight downward hook.

*Color.*—Early stage close to 184B; aging close to 178B.

H. Winter hardiness: Average.

I claim:

1. A new and distinct rose cultivar of the hybrid tea class, substantially as herein shown and described.

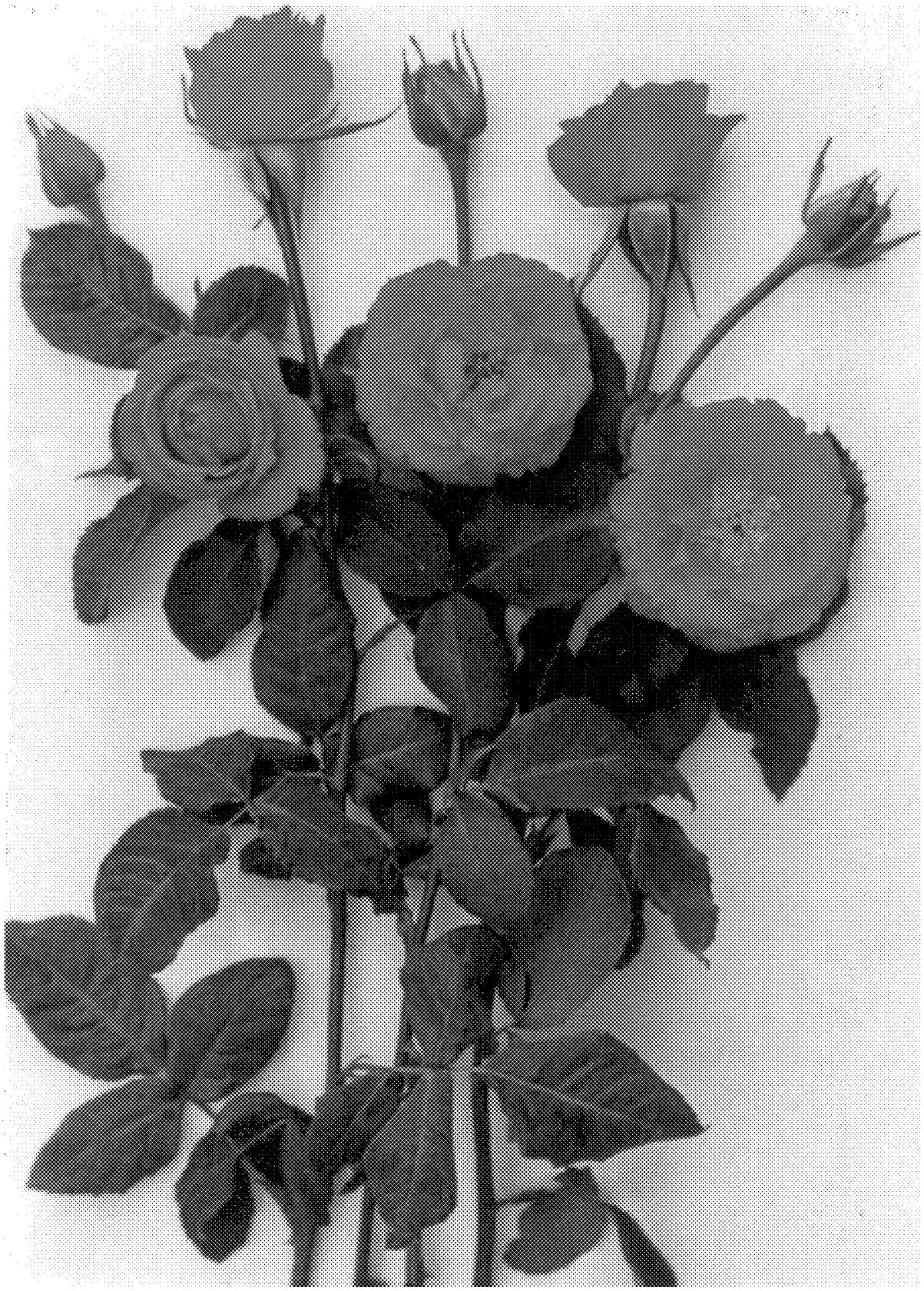

* * * * *